United States Patent
Qin et al.

(10) Patent No.: US 12,115,004 B2
(45) Date of Patent: Oct. 15, 2024

(54) METHOD AND APPARATUS FOR PROCESSING PHYSIOLOGICAL SIGNALS AND NON-TRANSITORY COMPUTER-READABLE MEDIUM

(71) Applicants: Luyun Qin, Beijing (CN); Ke Liao, Beijing (CN); Xiaojing Fan, Beijing (CN); Jinting Hou, Beijing (CN); Wei Wang, Beijing (CN)

(72) Inventors: Luyun Qin, Beijing (CN); Ke Liao, Beijing (CN); Xiaojing Fan, Beijing (CN); Jinting Hou, Beijing (CN); Wei Wang, Beijing (CN)

(73) Assignee: Ricoh Company, Ltd., Tokyo (JP)

( * ) Notice: Subject to any disclaimer, the term of this patent is extended or adjusted under 35 U.S.C. 154(b) by 499 days.

(21) Appl. No.: 17/445,866

(22) Filed: Aug. 25, 2021

(65) Prior Publication Data
US 2022/0061771 A1 Mar. 3, 2022

(30) Foreign Application Priority Data

Aug. 27, 2020 (CN) .......................... 202010880499.5

(51) Int. Cl.
*A61B 5/00* (2006.01)
(52) U.S. Cl.
CPC .......... *A61B 5/7232* (2013.01); *A61B 5/7203* (2013.01); *A61B 5/7225* (2013.01)
(58) Field of Classification Search
CPC .... A61B 5/7232; A61B 5/7203; A61B 5/7225
USPC ........................................................ 600/300
See application file for complete search history.

(56) References Cited

U.S. PATENT DOCUMENTS

| | | | | |
|---|---|---|---|---|
| 5,205,295 | A * | 4/1993 | Del Mar | A61B 5/337 600/524 |
| 5,355,891 | A * | 10/1994 | Wateridge | A61B 5/335 600/521 |
| 6,152,883 | A * | 11/2000 | Blanchett | A61B 5/7232 600/509 |
| 7,860,561 | B1 * | 12/2010 | Modarres | A61B 5/372 600/544 |
| 2010/0298676 | A1 * | 11/2010 | Addison | A61B 5/726 600/324 |
| 2013/0137937 | A1 * | 5/2013 | Dziubinski | A61B 5/72 600/300 |
| 2018/0078219 | A1 * | 3/2018 | Selvaraj | A61B 5/7221 |
| 2019/0339224 | A1 * | 11/2019 | Bhavaraju | A61B 5/14532 |
| 2020/0138291 | A1 * | 5/2020 | Bardy | A61B 5/259 |
| 2020/0245950 | A1 * | 8/2020 | Liang | A61B 5/01 |

FOREIGN PATENT DOCUMENTS

| | | | | |
|---|---|---|---|---|
| CN | 104739509 B | * | 11/2017 | ........... A61B 5/0002 |
| EP | 3643228 A1 | * | 4/2020 | ............. A61B 5/055 |
| WO | WO-2015100910 A1 | * | 7/2015 | ........... A61B 5/0002 |

* cited by examiner

*Primary Examiner* — Michael J Lau
(74) *Attorney, Agent, or Firm* — IPUSA, PLLC

(57) ABSTRACT

Disclosed are a method and apparatus for processing physiological signals. The method is inclusive of steps of obtaining the physiological signals; grouping the physiological signals based on their sampling frequencies and/or generation mechanisms, so as to acquire grouping results; and compressing, based on the grouping results, each group of physiological signals.

13 Claims, 9 Drawing Sheets

ECG DATA    BP DATA

METHOD AND APPARATUS FOR PROCESSING PHYSIOLOGICAL SIGNALS AND NON-TRANSITORY COMPUTER-READABLE MEDIUM

BACKGROUND OF THE INVENTION

1. Field of the Invention

The present disclosure relates to the field of biomedical equipment, and more particularly, a method and apparatus for processing physiological signals as well as a non-transitory computer-readable medium.

2. Description of the Related Art

With the advancement of technology and the development of smaller sensors, a body area network (BAN) composed of physical sign sensors and their devices has been used in telemedicine and long-term health care for conducting remote and long-run collection of physical sign signals. This kind of work mode is becoming more and more widely accepted.

Generally speaking, physical sign sensors and the physical sign signals collected by them have the following characteristics.

1. High Frequency Based Acquisition

High-frequency based acquisition is for meeting the basic requirements of physical sign signal collection. For example, the frequency for collecting physiological signals such as pulses, electrocardiogram (ECG) signals, and so on is usually above 100 Hz. In order to satisfy the demands of clinical use, a frequency above 500 Hz is required in actuality when collecting the physiological signals like pulses, ECG signals, etc.

2. Wireless Transmission

Physical sign sensors and acquisition devices usually adopt wireless network based transmission to meet the needs of comfort and portability. The application of a body area network based on long-term high-frequency collection is very sensitive to the overhead and bandwidth of wireless network based transmission.

As a result, physical sign sensors as well as physical sign signal acquisition devices and systems must be designed to perform compression on the collected original physical sign signals before conducting data transmission so as to decrease the data transmission amount of the related wireless network, thereby reducing power and bandwidth consumption.

The existing compression algorithms relating to physiological signals are basically divided into two categories: lossless physiological signal compression and lossy physiological signal compression. Lossless physiological signal compression mainly utilizes general signal compression approaches such as Huffman coding, arithmetic coding, dictionary-based Lempel-Ziv (LZ) coding, and the combination of at least two of them. Lossy physiological signal compression may adopt approximation approaches like polyline approximation and sector (fan-shaped) region approximation, transform approaches such as wavelet transform and principal component transform, etc.

By making use of a general lossless physiological signal compression algorithm, data can be compressed to a certain extent, but because grammar-based signal compression is adopted in this case, the upper limit of compression ratio is restricted by information entropy, and the data cannot be effectively compressed. Additionally, by employing a lossy physiological signal compression algorithm like polyline approximation, sector region approximation, wavelet transform, etc. to perform approximation or transformation on signals, it is possible to dramatically improve the performance of data compression. However, this type of approach may damage the fidelity of information; that is, the signal fidelity tends to decrease with the increase of the compression ratio. When such an approach is adopted, a lot of detailed signals will be lost after signal restoration, so this is unacceptable in situations where higher signal fidelity is required.

SUMMARY OF THE INVENTION

In light of the above, the present disclosure provides at least a method and apparatus for processing physiological signals, by which signal fidelity and data compression can be well balanced.

According to a first aspect of the present disclosure, a method of processing physiological signals is provided that may include steps of obtaining the physiological signals; grouping the physiological signals based on their sampling frequencies and/or generation mechanisms, so as to acquire grouping results; and compressing, based on the grouping results, each group of physiological signals.

Moreover, in accordance with at least one embodiment, before the step of grouping the physiological signals based on their sampling frequencies and/or generation mechanisms, the method may further include steps of identifying missing values caused by artifacts in the physiological signals; perform filling on the missing values; and attaining the sampling frequencies of the physiological signals after filling.

Furthermore, in accordance with at least one embodiment, the physiological signals generated by the same body organ and/or the same physiological activity have the same generation mechanism, and the physiological signals with the same mechanism are in the same group.

Additionally, in accordance with at least one embodiment, the step of performing filling on the missing values may be inclusive of a step of conducting filling with respect to the missing values by using numbers.

Furthermore, in accordance with at least one embodiment, the step of compressing, based on the grouping results, each group of physiological signals may contain steps of procuring a data characteristic of each group of physiological signal; and determining a compression baseline based on the data characteristic, and utilizing the compression baseline to carry out compression in regard to the same group of physiological signals.

Moreover, in accordance with at least one embodiment, the determining a compression baseline based on the data characteristic may involve any one of steps of adopting, when values of a group of physiological signals change within a predetermined range, an average or median value of the same group of physiological signals to serve as the compression baseline; employing, when function fitting is able to be performed on a group of physiological signals, a function acquired by performing function fitting on the same group of physiological signals to serve as the compression baseline; and adopting original physiological signals during a data cycle (a period of time) to serve as the compression baseline.

Additionally, in accordance with at least one embodiment, in a case where the original physiological signals during a data cycle are adopted to serve as the compression baseline, the method may further include a step of updating the compression baseline after the data cycle of the physiological signals changes.

Furthermore, in accordance with at least one embodiment, the step of compressing, based on the grouping results, each group of physiological signals may be inclusive of a step of determining, based on data cycles of each group of physiological signals, a compression window corresponding to the same group of physiological signals, and carrying out, based on the compression window corresponding to the same group of physiological signals, compression with respect to the same group of physiological signals.

Moreover, in accordance with at least one embodiment, in a case where the data cycles of each group of physiological signals contains only t1, the size of the compression window is determined by n=k*t1, and in a case where the data cycles of each group of physiological signals includes t1, t2, . . . tm, the size of the compression window is determined by n=k*[t1, t2, . . . , tm]. Here, n refers to the size of the compression window; [t1, t2, . . . , tm] is the least common multiple of the data cycles t1, t2, . . . , tm; and m and k are integers greater than 1.

According to a second aspect of the present disclosure, an apparatus for processing physiological signals is provided that may include an obtainment part configured to obtain the physiological signals; a grouping part configured to group the physiological signals based on their sampling frequencies and/or generation mechanisms, so as to acquire grouping results; and a compression part configured to compress, based on the grouping results, each group of physiological signals.

Moreover, in accordance with at least one embodiment, the apparatus may further include an identification part configured to identify missing values caused by artifacts in the physiological signals; a filling part configured to perform filling on the missing values; and a sampling frequency attainment part configured to attain the sampling frequencies of the physiological signals after filling.

Furthermore, in accordance with at least one embodiment, the compression part may contain an subpart configured to acquire a data acquisition characteristic of each group of physiological signal, and determine a compression baseline based on the data characteristic; and a processing subpart configured to utilize the compression baseline to carry out compression in regard to the same group of physiological signals.

Moreover, in accordance with at least one embodiment, the acquisition subpart may be concretely configured to conduct any one of adopting, when values of a group of physiological signals change within a predetermined range, an average or median value of the same group of physiological signals to serve as the compression baseline; employing, when function fitting is able to be performed on a group of physiological signals, a function acquired by performing function fitting on the same group of physiological signals to serve as the compression baseline; and adopting original physiological signals during a data cycle to serve as the compression baseline.

Additionally, in accordance with at least one embodiment, the compression part may further include a compression window determination subpart configured to determine, based on data cycles of each group of physiological signals, a compression window corresponding to the same group of physiological signals. In this case, the processing subpart may be configured to carry out, based on the compression baseline and/or the compression window corresponding to the same group of physiological signals, compression with respect to the same group of physiological signals.

According to a third aspect of the present disclosure, an apparatus for processing physiological signals is provided that may be inclusive of a processor and a memory (i.e., a storage) connected to the processor. The memory stores a processor-executable program (i.e., a computer-executable program) that, when executed by the processor, may cause the processor to conduct the method of processing physiological signals.

According to a fourth aspect of the present disclosure, a computer-executable program and a non-transitory computer-readable medium are provided. The computer-executable program may cause a computer to perform the method of processing physiological signals. The non-transitory computer-readable medium stores computer-executable instructions (i.e., the processor-executable program) for execution by a computer involving a processor. The computer-executable instructions, when executed by the processor, may render the processor to carry out the method of processing physiological signals.

Compared to the conventional technology, the method and apparatuses for processing physiological signals can group, before compressing the physiological signals obtained, the physiological signals on the basis of their sampling frequencies and/or generation mechanisms, and then conduct compression pertaining to the physiological signals in terms of groups. The technical solution according to the embodiments may provide the feasibility for obtaining better compression results because the correlations between the physiological signals are considered when performing compression. In addition, compared with the traditional approach of clustering physiological signals based on data similarity, because the technical solution does not require a complex calculation process and algorithm when grouping the physiological signals, it is possible to save computational resources, achieve data compression to a greater extent, and maintain the fidelity of the physiological signals.

DESCRIPTION OF THE EMBODIMENTS

In order to let a person skilled in the art better understand the present disclosure, hereinafter, the embodiments of the present disclosure are concretely described with reference to the drawings. However, it should be noted that the same symbols, that are in the specification and the drawings, stand for constructional elements having basically the same function and structure, and the repetition of the explanations to the constructional elements is omitted.

In the embodiments of the present disclosure, at least a method and apparatus for processing physiological signals are provided by which it is possible to well balance signal fidelity and data compression.

First Embodiment

In this embodiment, a method of processing physiological signals is provided.

Figure 1:
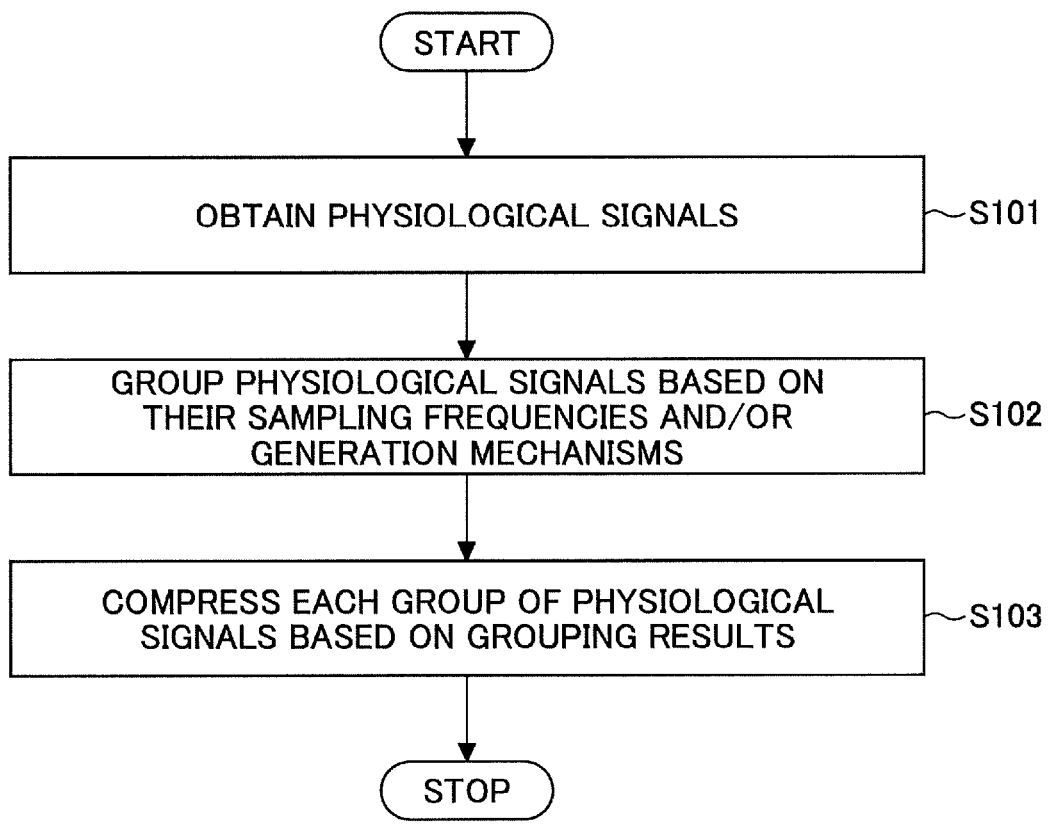
FIG. 1 is a flowchart of a method of processing physiological signals according to a first embodiment of the present disclosure.

FIG. 1 is a flowchart of the method of processing physiological signals. As shown in FIG. 1, the method is inclusive of STEPS S101 to S102.

STEP S101 is obtaining physiological signals. Here, the physiological signals may be signals collected by physical sign sensors, and include but not be limited to ECG signals, BP signals, pulse signals, PPG (photoplethysmogram) signals, etc.

In STEP S102, the physiological signals are grouped on the basis of their sampling frequencies and/or generation mechanisms.

In the medical field, there are correlations between physiological signals. As presented in FIG. 2 that illustrates an example of grouping physiological signals, the electrical activity of a heart may produce ECG signals, while the physical activity of the heart may generate BP signals, pulse signals, PPG signals, etc. Because all these signals are produced by the heart, there are correlations between them. Generally speaking, signals with correlation usually have the same cycle and change trend; in addition, physiological signals with the same sampling frequency also have the same cycle and change trend. As such, when grouping physiological signals, it is possible to carry out grouping in regard to them based on their sampling frequencies and/or generation mechanisms.

Here, it can be considered that the generation mechanisms of the physiological signals produced by the same body organ are the same; the generation mechanisms of the physiological signals generated by the same physiological activity are the same; or the generation mechanisms of the physiological signals produced by the same body organ and the same physiological activity are the same. On the grounds of this, in this embodiment, the physiological signals with the same sampling frequency and the same generation mechanism may be grouped into the same group; the physiological signals with the same sampling frequency may be grouped into the same group; or the physiological signals with the same generation mechanism may be grouped into the same group.

STEP S103 is compressing each group of physiological signals according to the grouping results of STEP S102.

In this embodiment, before compressing the physiological signals obtained, the physiological signals may be grouped on the basis of their sampling frequencies and/or generation mechanisms, and then compression with respect to the physiological signals can be performed by group. By taking account of the correlations between the physiological signals when conducting compression, the technical solution in accordance with this embodiment may provide the feasibility for acquiring better compression results. Additionally, compared with the existing approach of clustering physiological signals based on data similarity, because the technical solution does not need a complicated calculation process and algorithm when grouping the physiological signals, it is possible to save computational resources, achieve data compression to a greater extent, and maintain the fidelity of the physiological signals.

Second Embodiment

Figure 3:
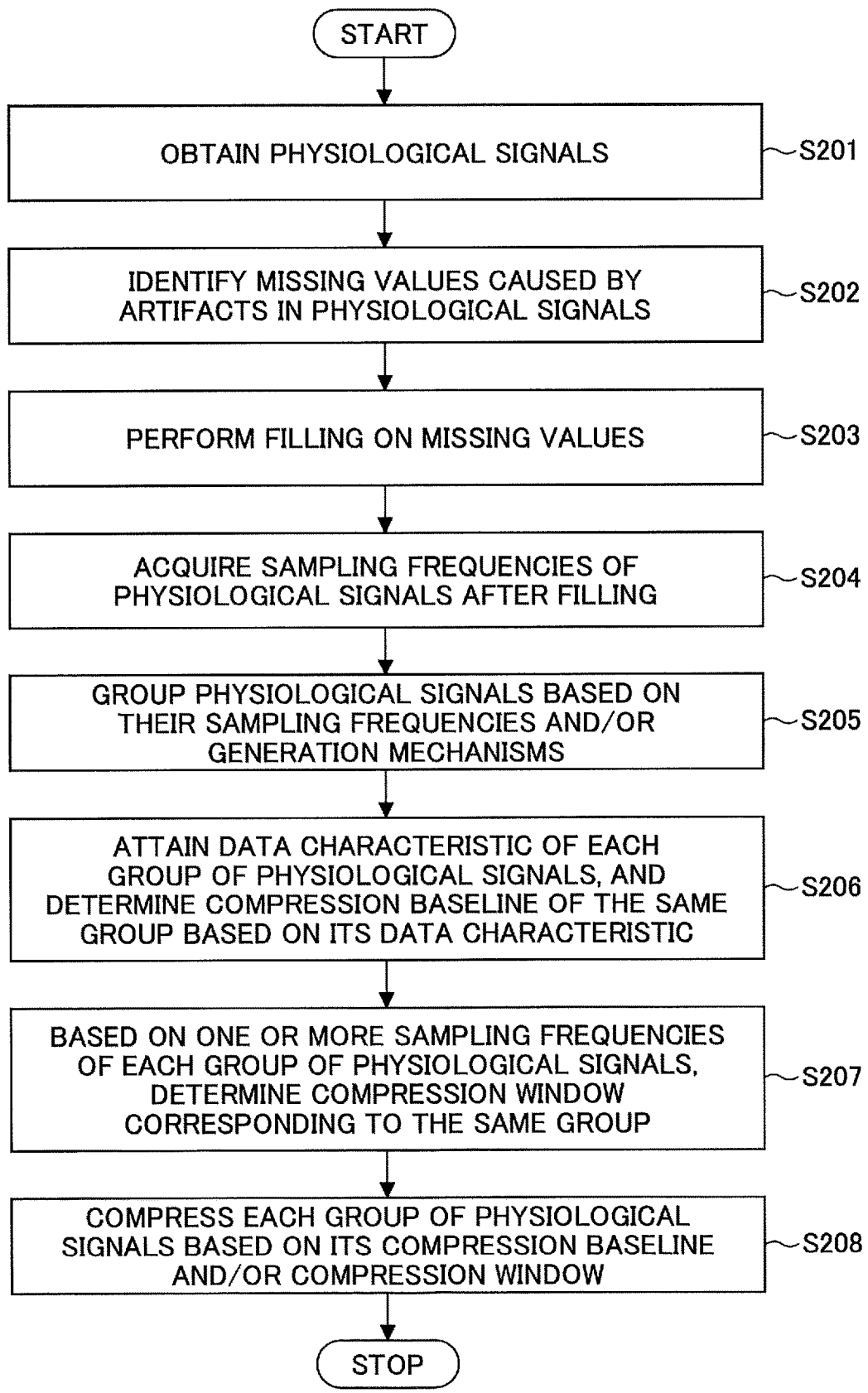
FIG. 3 is a flowchart of another method of processing physiological signals in accordance with a second embodiment of the present disclosure.

Another method of processing physiological signals is provided in this embodiment, whose flowchart is illustrated in FIG. 3. As shown in FIG. 3, the other method contains STEPS S201 to S208.

STEP S201 is obtaining physiological signals. Here, the physiological signals may be signals collected by physical sign sensors, and include but not be limited to ECG signals, BP signals, pulse signals, PPG signals, etc.

In STEP S202, missing values caused by artifacts in the physiological signals are identified. In general, when using a monitor to acquire physiological signals, it can be regarded that a physiological signal generated when the interference parameter of the monitor is greater than a predetermined threshold is a missing value caused by an artifact. In this way, it is possible to detect data holes in the physiological signals, so as to avoid the influence of the data holes on the subsequent compression process.

STEP S203 is carrying out filling with respect to the missing values. Specifically, the missing values can be filled with numbers, so that the data holes are able to be filled, the influence of data loss on the follow-on compression process can be avoided, and the compression quality can be improved.

In STEP S204, the sampling frequencies of the physiological signals after filling are attained.

STEP S205 is grouping the physiological signals on the basis of their sampling frequencies and/or generation mechanisms.

Figure 2:
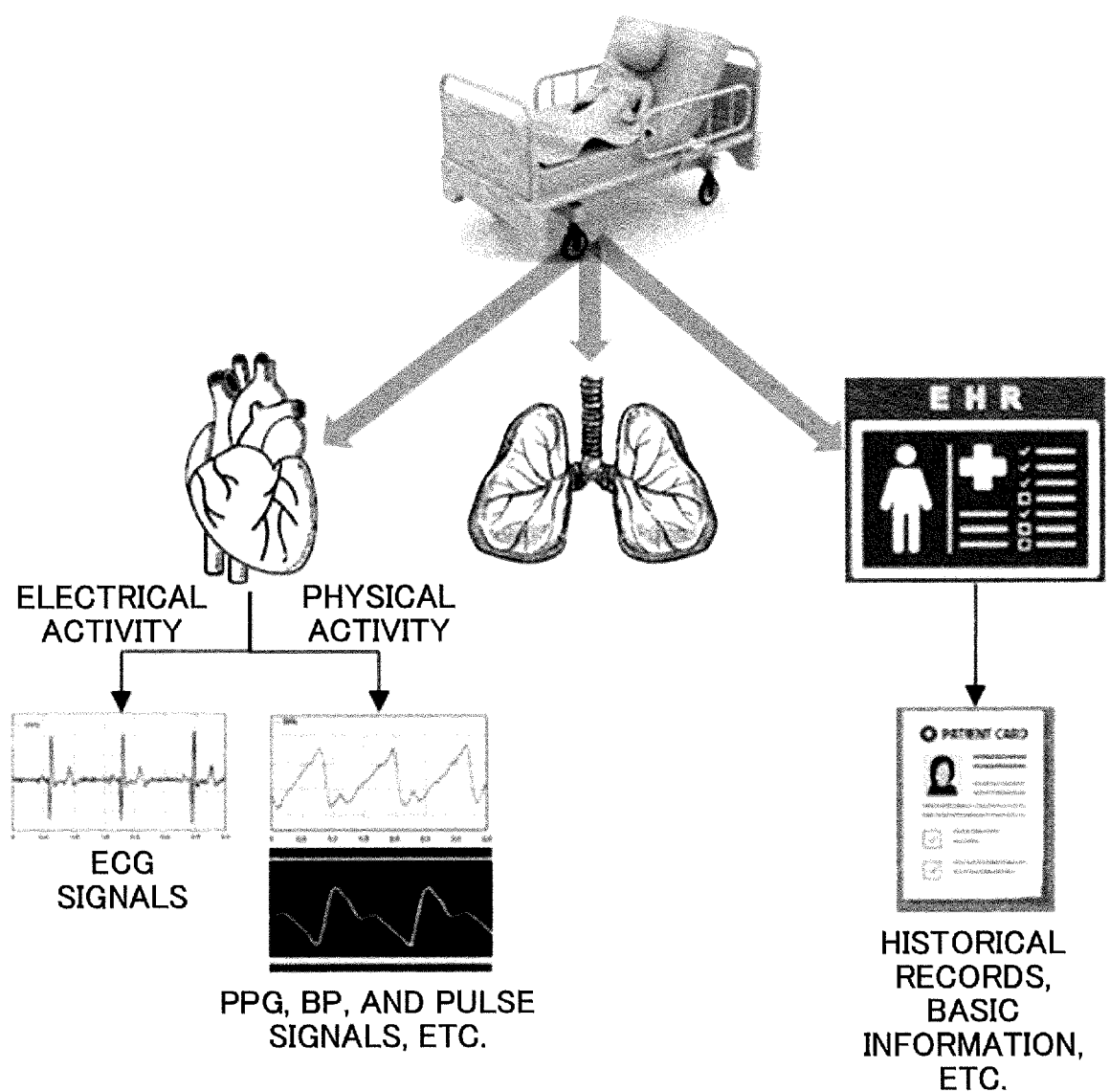
FIG. 2 illustrates an example of performing grouping on physiological signals.

In the medical field, there are correlations between physiological signals. As shown in FIG. 2 that illustrates an example of grouping physiological signals, the electrical activity of a heart may produce ECG signals, while the physical activity of the heart may generate BP signals, pulse signals, PPG signals, etc. Because all these signals are produced by the heart, there are correlations between them. Generally speaking, signals with correlation usually have the same cycle and change trend; in addition, physiological signals with the same sampling frequency also have the same cycle and change trend. On this account, when physiological signals are grouped, it is possible to conduct grouping pertaining to them on the basis of their sampling frequencies and/or generation mechanisms.

Here, it can be considered that the generation mechanisms of the physiological signals produced by the same body organ are the same; the generation mechanisms of the physiological signals generated by the same physiological activity are the same; or the generation mechanisms of the physiological signals produced by the same body organ and the same physiological activity are the same. In light of this, in this embodiment, the physiological signals with the same sampling frequency and the same generation mechanism may be grouped into the same group; the physiological signals with the same sampling frequency may be grouped into the same group; or the physiological signals with the same generation mechanism may be grouped into the same group.

STEP S206 is attaining the data characteristic of each group of physiological signals, and determining a compression baseline corresponding to the same group of physiological signals on the basis of the data characteristic. Generally speaking, when performing compression on physiological signals, one important step is determining a compression baseline.

In this embodiment, based on the data characteristic of each group of physiological signals, it is possible to determine, in different ways, compression baselines of physiological signals for different types of physiological signals, so that suitable compression baselines can be chosen for different types of physiological signals, and the efficiency of compression can be ameliorated.

In some examples, when the values of a group of physiological signals fluctuate within a predetermined range, for example, the pulses may fluctuate within a very small range, the average or median value of this group of physiological signals may be used as a compression baseline. Moreover, in some examples, when function fitting is able to be performed on a group of physiological signals, a function acquired by conducting function fitting in regard to this group of physiological signals may serve as a compression baseline. Additionally, in some examples, it is possible to let the original physiological signals during a data cycle (e.g., a previous data cycle) to be a compression baseline, so that the process of compression can be speeded up because there is no need to carry out a complicated fitting process. In general, physiological signals may be presented as waveforms, and a complete is the data cycle of the physiological waveform signals.

Figure 4:
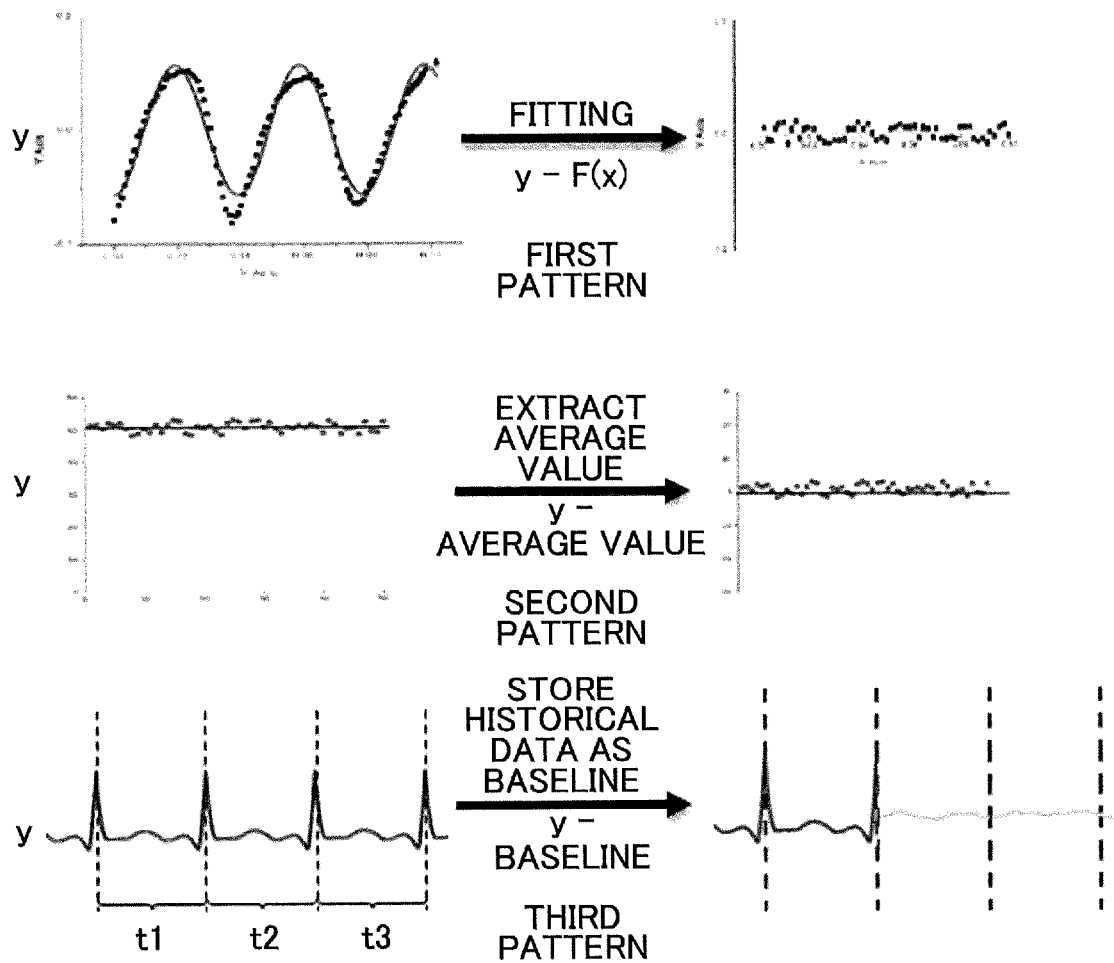
FIG. 4 shows an example of determining compression baselines.

FIG. 4 shows an example of determining compression baselines. As illustrated in FIG. 4, there are three groups (i.e., a first, second, and third group) of physiological signals with different patterns (i.e., a first, second, and third pattern). The first group of physiological signals with the first pattern refers to physiological signals on which function fitting is easily performed. It is possible to carry out function fitting with respect to the first group of physiological signals so as to acquire a function, and let the function be a compression baseline so as to conduct differential compression. The second group of physiological signals with the second pattern represents physiological signals whose values change within a very small range (e.g., a predetermined range). The average or median value of the second group of physiological signals can serve as a compression baseline for conducting differential compression. The third group of physiological signals with the third pattern stands for physiological signals that do not have an obvious characteristic. In this case, it is possible to adopt the original physiological signals during a data cycle to function as a compression baseline based on which differential compression will be conducted. The original physiological signals serving as the compression baseline may be those in the e third group of physiological signals, or the historical data before the third group of physiological signals. However, when the historical data before the third group of physiological signals is adopted, the sampling frequency and generation mechanism of the historical data need to be the same as those of the third group of physiological signals.

In actuality, many physiological signals are not proper to carry out function fitting. On that account, for the sake of convenience, actually it is possible to utilize the approaches of determining the baselines of the second and third group of physiological signals with the second and third pattern. However, the present disclosure is not limited to this.

Moreover, due to the physical characteristics of a human body, the data cycle of physiological signals is not always constant. Generally, it may remain constant during a short period of time. However, some factors such as an electric knife used during surgery and the like can affect the data cycle. Accordingly, in a case where the original physiological signals during a previous data cycle are adopted to serves as a compression baseline, after the original physiological signals during a data cycle before the current data cycle are acquired, it is necessary to first determine whether the data cycle has changed. If the data cycle has changed, then it is also necessary to procure a new compression baseline on the basis of the original physiological signals during a new data cycle, i.e., carry out a compression baseline update process.

Figure 5:
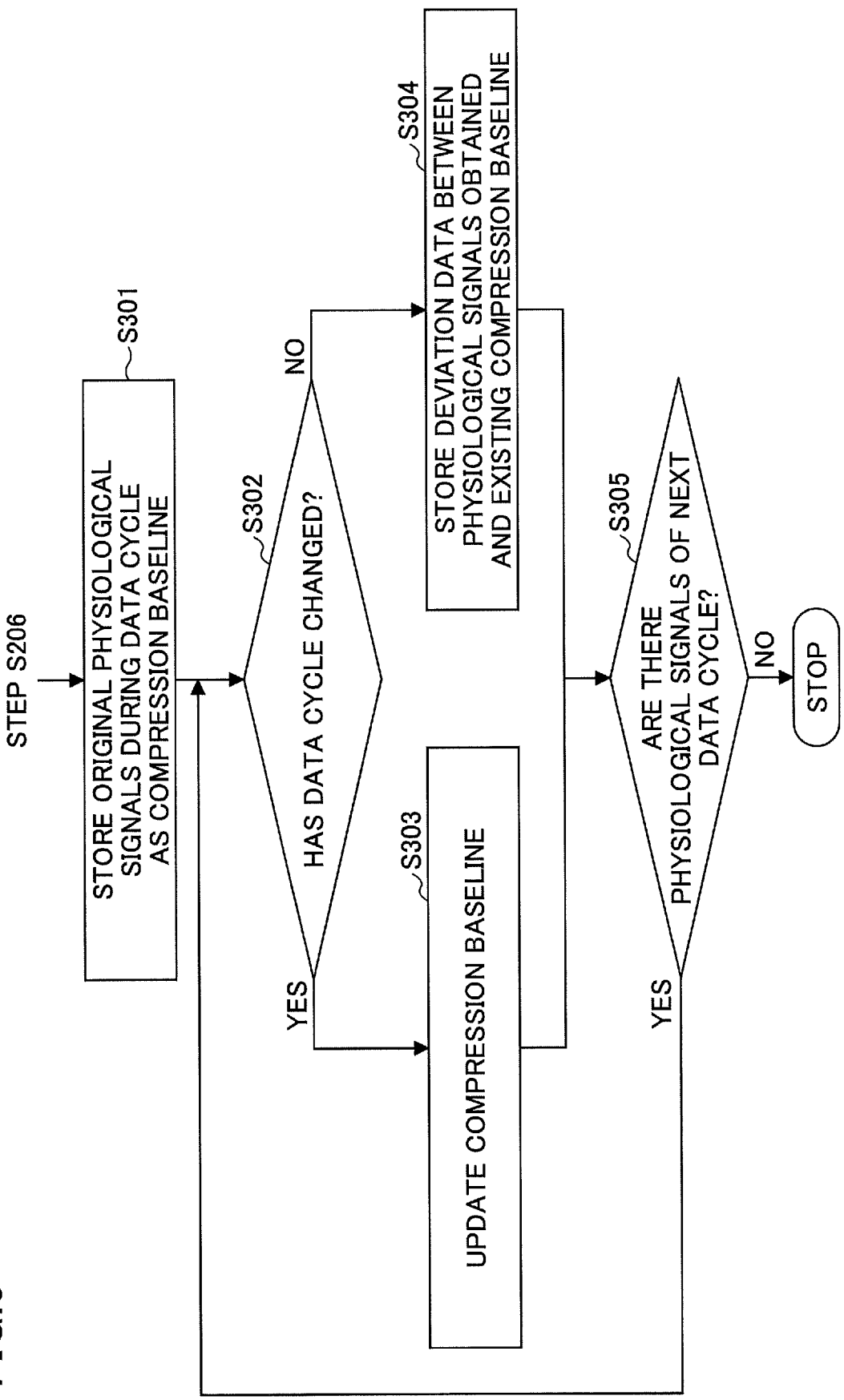
FIG. 5 is an exemplary process of updating a compression baseline.

FIG. 5 is an exemplary process (also called an update process) of updating a compression baseline. As presented in FIG. 5, the update process is inclusive of STEPS S301 to S305.

STEP S301 is storing the original physiological signals during a data cycle to serve as a compression baseline.

In STEP S302, it is determined whether the data cycle has changed. If it has changed, then the update process goes to STEP S304.

STEP S303 is updating the compression baseline. Specifically, the original physiological signals during an updated data cycle are used as a new compression baseline.

In STEP S304, the deviation data between the physiology signals obtained and an existing compression baseline is stored.

STEP S305 is determining whether there is a next data cycle during which physiology signals have been collected. If there exists such a next data cycle, then the update process goes back to STEP S302; otherwise, the update process stops.

Referring again to FIG. 3; STEP S207 is determining, based on the data cycles (i.e., one or more data cycles) of each group of physiological signals, a compression window corresponding to the same group.

When compressing physiological signals, another important step is determining a compression window. Different physiological signals have different data cycles. In this embodiment, it is possible to determine, based on the data cycles of each group of physiological signals, a compression window corresponding to the same group of physiological signals, and compress the physiological signals in same group on the basis of the compression window determined.

In a case where the data cycles of each group of physiological signals includes only t1, the size of the compression window may be determined by n=k*t1, and in a case where the data cycles of each group of physiological signals contains t1, t2, ..., tm, the size of the compression window may be determined by n=k*[t1, t2, ..., tm]. Here, n refers to the size the compression window; [t1, t2, ..., tm] is the least common multiple of the data cycles t1, t2, ..., tm; and m and k are integers greater than 1.

Figure 6:
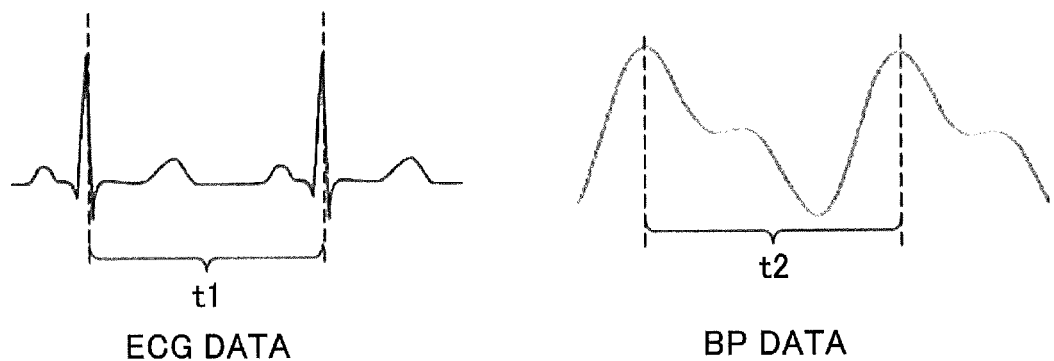
FIG. 6 presents ECG data and BP (blood pressure) data having different data cycles.

FIG. 6 presents ECG data and BP data having different data cycles. As shown in FIG. 6, the ECG data and the BP data have a data cycle t1 and a data cycle t2, respectively. Even if these two kinds of physiological signals come from the same patient, their data cycles may be different because their generation mechanisms and/or sampling frequencies are different.

When the two types of physiological signals presented in FIG. 6 are taken as an example, if the physiological signals collected contain only one kind of data cycle, for example, include only ECG signals or BP signals, then the size of the related compression window can be determined as $n=k*t1$ or $n=k*t2$ ($k>1$), and if there are multiple types of periodic signals (e.g., ECG signals and BP signals) in the physiological signals collected, then the size of the relevant compression window can be calculated by $n=k*[t1, t2]$. Here, $k>1$, and $[t1, t2]$ is the least common multiple of t1 and t2.

In STEP S208 of FIG. 3, compression is carried out with respect to each group of physiological signals on the basis of the compression baseline and/or the compression window corresponding to the same group of physiological signals.

After the compression baseline and/or the compression window are determined, each group of physiological signals can be compressed. This embodiment can select an appropriate compression baseline and/or a compression window for each group of physiological signals, thereby being capable of reducing the amount of calculation and improving the compression efficiency and compression quality.

Third Embodiment

Figure 7:
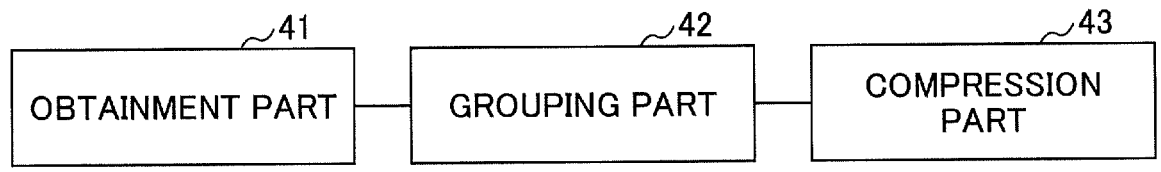
FIG. 7 is a block diagram of an apparatus for processing physiological signals according to a third embodiment of the present disclosure.

According to one aspect of this embodiment, an apparatus for processing physiological signals is provided. FIG. 7 is a block diagram of the apparatus. As presented in FIG. 7, the apparatus contains an obtainment part 41, a grouping part 42, and a compression part 43. Of the apparatus may also include other parts as needed.

The apparatus for processing physiological signals may be configured to implement the method of processing physiological signals in accordance with the first embodiment. In particular, the obtainment part 41, the grouping part 42, and the compression part 42 are able to be configured to carry out STEP S101 to S103 of FIG. 1, respectively.

Also, it should be pointed out that for the reason that STEPS S101 to S103 of FIG. 1 have been minutely described in the first embodiment, the details of them are omitted in this embodiment.

Figure 8:
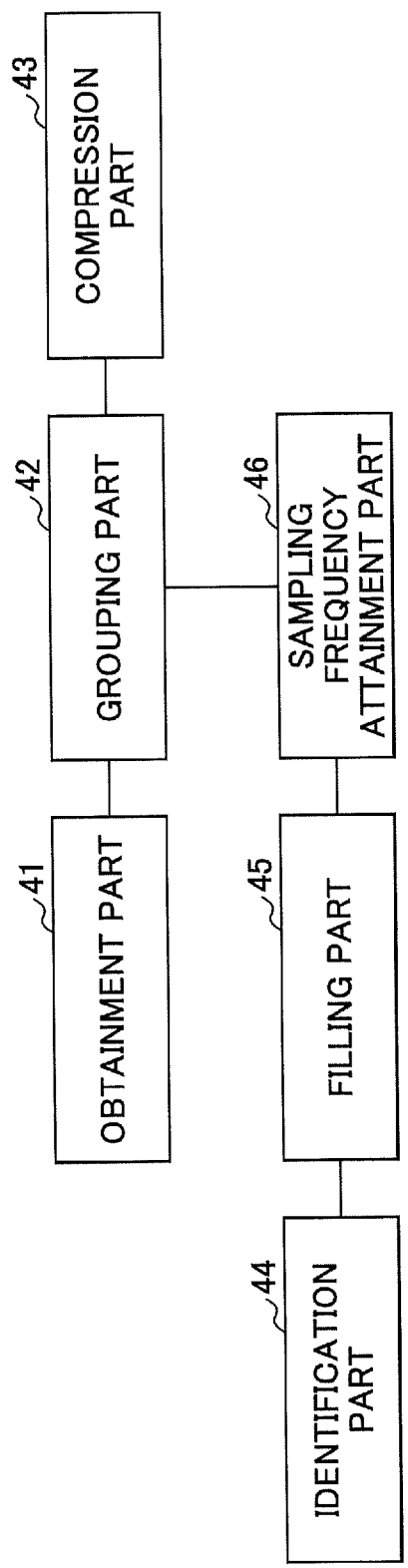
FIG. 8 shows another structure of the apparatus for processing physiological signals.

According to another aspect of this embodiment, another apparatus for processing physiological signals is provided. FIG. 8 is a block diagram of the other apparatus. As shown in FIG. 8, the other apparatus is inclusive of an obtainment part 41, a grouping part 42, and a compression part 43, an identification part 44, a filling part 45, and a sampling frequency attainment part 46. Of course, the other apparatus may also include other parts as needed.

Figure 9:
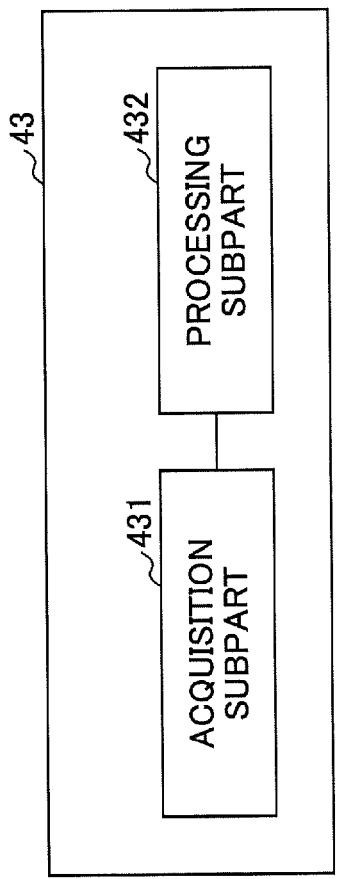
FIG. 9 illustrates a block diagram of a compression part.

In an example, the compression part 43 may be configured to contain an acquisition subpart 431 and a processing subpart 432, as illustrated in FIG. 9.

Figure 10:
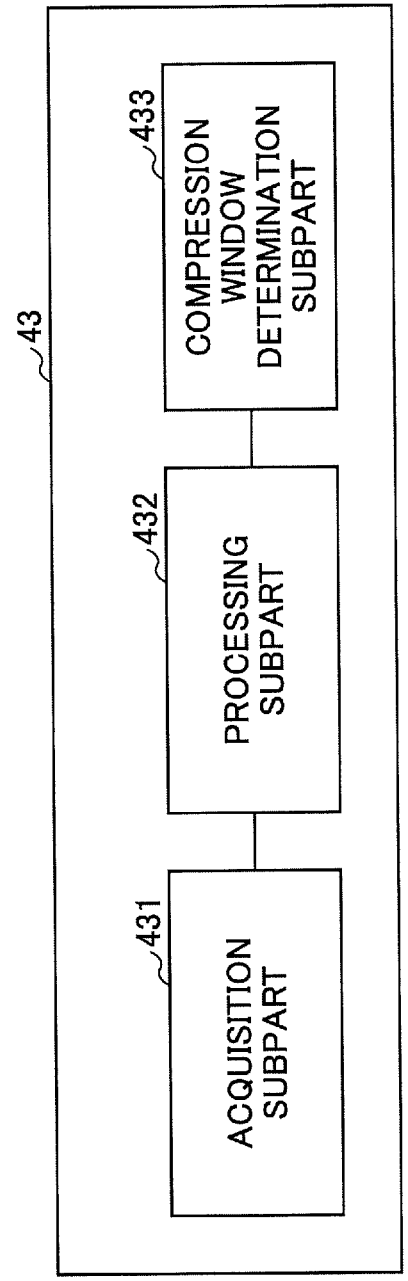
FIG. 10 presents another structure of the compression part.

In another example, the compression part 43 may be configured to include an acquisition subpart 431, a processing subpart 432, and a compression window determination subpart 433, as presented in FIG. 10.

The other apparatus for processing physiological signals may be configured to implement the other method of processing physiological signals in accordance with the second embodiment.

Specially, the obtainment part 41, the identification part 44, the filling part 45, the sampling frequency attainment part 46, and grouping part 42 of the other apparatus for processing physiological signals are able to be configured to conduct STEP S201 to S205 in FIG. 3, respectively.

Furthermore, the acquisition subpart 431 and the processing subpart 432 of the compression part 43 shown in FIG. 9 may be configured to perform STEP S206 and STEP S208 of FIG. 3, respectively. Here it should be noted that in this case, the processing subpart 432 is configured to compress each group of physiological signals on the basis of the determined compression baseline corresponding to the same group of physiological signals in STEP 208 of FIG. 3.

On the other hand, the acquisition subpart 431, the compression window determination subpart 433, and the processing subpart 432 of the compression part 43 presented in FIG. 10 may be configured to conduct STEPS S206 to S208 of FIG. 3, respectively. Here it should be emphasized that in this case, the processing subpart 432 is configured to compress each group of physiological signals on the basis of the determined compression baseline and/or compression window corresponding to the same group of physiological signals in STEP 208 of FIG. 3.

Also, it should be pointed out that for the reason that STEPS S201 to S208 of FIG. 3 have been concretely described in the second embodiment, the details of them are omitted here for the sake of convenience.

In this embodiment, before compressing the physiological signals obtained, the physiological signals may be grouped on the basis of their sampling frequencies and/or generation mechanisms, and then compression with respect to the physiological signals can be performed by group. By taking account of the correlations between the physiological signals when conducting compression, the technical solution in accordance with this embodiment may provide the feasibility for acquiring better compression results. Additionally, compared with the existing approach of clustering physiological signals based on data similarity, because the technical solution does not need a complicated calculation process and algorithm when grouping the physiological signals, it is possible to save computational resources, achieve data compression to a greater extent, and maintain the fidelity of the physiological signals.

Fourth Embodiment

In this embodiment, according to one aspect, an apparatus 50 for processing physiological signals is provided that may be configured to conduct the method of processing physiological signals in accordance with the first or second embodiment.

Figure 11:
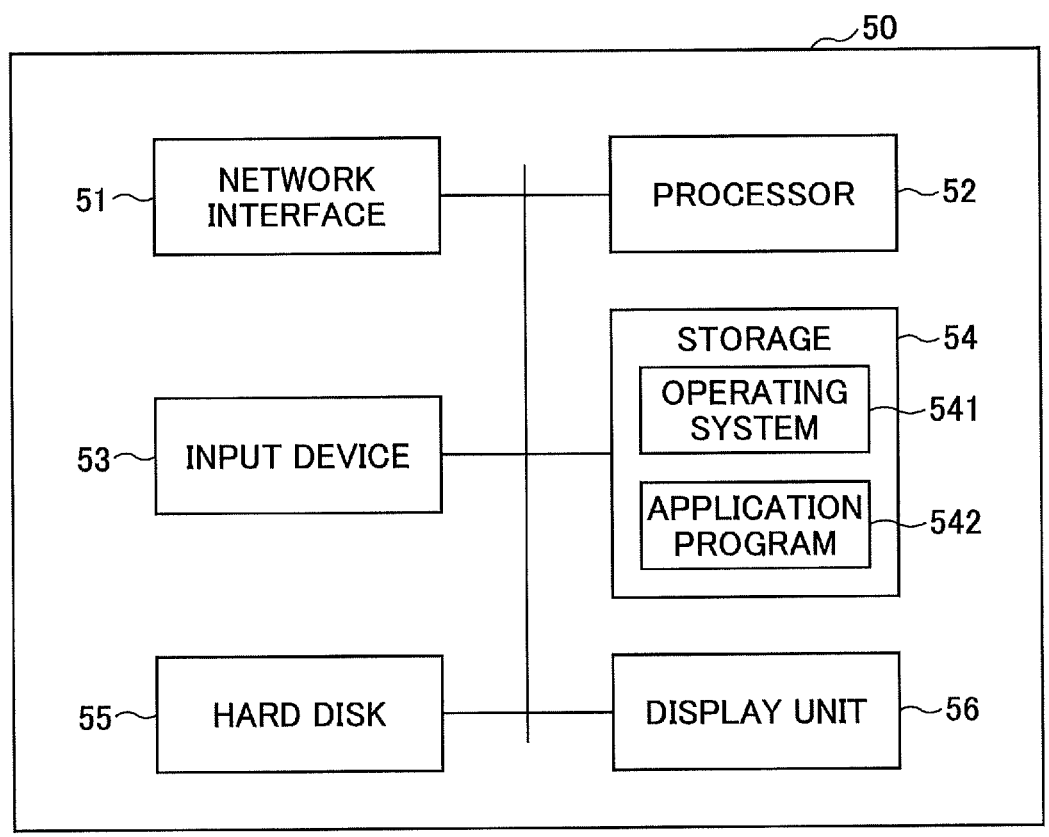
FIG. 11 is a block diagram of another apparatus for processing physiological signals in accordance with a fourth embodiment of the present disclosure.

FIG. 11 is a block diagram of the apparatus 50 according to this embodiment. As presented in FIG. 11, the apparatus 50 may contain a processor 52 and a storage 54 connected to the processor 52.

The processor 52 may be configured to execute a computer program (i.e., computer-executable instructions) stored in the storage 54 so as to fulfill the method of processing physiological signals in accordance with the first or second embodiment. The processor 52 may adopt any one of the conventional processors in the related art.

The storage 54 may store an operating system 541, an application program 542 (i.e., the computer program), the relating data, and the intermediate results generated when the processor 52 conducts the computer program, for example. The storage 54 may use any one of the existing storages in the related art.

In addition, as shown in FIG. 11, the apparatus 50 may further include a network interface 51, an input device 53, a hard disk 55, and a display unit 56, which may also be achieved by using the conventional ones in the related art.

Moreover, according to another aspect of this embodiment, a computer-executable program and a non-transitory computer-readable medium are provided. The computer-executable program may cause a computer to perform the method of processing physiological signals according to the first or second embodiment. The non-transitory computer-readable medium may store computer-executable instructions (i.e., the computer program) for execution by a computer involving a processor. The computer-executable instructions may, when executed by the processor, render the processor to conduct the method of processing physiological signals in accordance with the first or second embodiment.

Because the steps of the method of processing physiological signals in accordance with the first or second embodiment have been concretely described above, the details of the steps are omitted here for the sake of convenience.

Here it should be noted that the above embodiments are just exemplary ones, and the specific structure and operation of them may not be used for limiting the present disclosure.

Furthermore, the embodiments of the present disclosure may be implemented in any convenient form, for example, using dedicated hardware or a mixture of dedicated hardware and software. The embodiments of the present disclosure may be implemented as computer software implemented by one or more networked processing apparatuses. The network may comprise any conventional terrestrial or wireless communications network, such as the Internet. The processing apparatuses may comprise any suitably programmed apparatuses such as a general-purpose computer, a personal digital assistant, a mobile telephone (such as a WAP or 3G, 4G, or 5G-compliant phone) and so on. Since the embodiments of the present disclosure may be implemented as software, each and every aspect of the present disclosure thus encompasses computer software implementable on a programmable device.

The computer software may be provided to the programmable device using any storage medium for storing processor-readable code such as a floppy disk, a hard disk, a CD ROM, a magnetic tape device or a solid state memory device.

The hardware platform includes any desired hardware resources including, for example, a central processing unit (CPU), a random access memory (RAM), and a hard disk drive (HDD). The CPU may include processors of any desired type and number. The RAM may include any desired volatile or nonvolatile memory. The HDD may include any desired nonvolatile memory capable of storing a large amount of data. The hardware resources may further include an input device, an output device, and a network device in accordance with the type of the apparatus. The HDD may be provided external to the apparatus as long as the HDD is accessible from the apparatus. In this case, the CPU, for example, the cache memory of the CPU, and the RAM may operate as a physical memory or a primary memory of the apparatus, while the HDD may operate as a secondary memory of the apparatus.

While the present disclosure is described with reference to the specific embodiments chosen for purpose of illustration, it should be apparent that the present disclosure is not limited to these embodiments, but numerous modifications could be made thereto by a person skilled in the art without departing from the basic concept and technical scope of the present disclosure.

The present application is based on and claims the benefit of priority of Chinese Patent Application No. 202010880499.5 filed on Aug. 27, 2020, the entire contents of which are hereby incorporated by reference.

What is claimed is:

1. A method of processing physiological signals, comprising:
   obtaining the physiological signals;
   grouping the physiological signals based on sampling frequencies and/or generation mechanisms, so as to acquire grouping results; and
   compressing, based on the grouping results, each group of physiological signals, the compressing including
   acquiring a data characteristic of a same group of physiological signals,
   determining a compression baseline based on the data characteristic, and
   utilizing the determined compression baseline to compress the same group of physiological signals,
   wherein the determining the compression baseline includes
   using an average or median value of the same group of physiological signals to serve as the compression baseline in response to a change in values of the same group of physiological signals within a predetermined range,
   adopting a function acquired by carrying out function fitting in regard to the same group of physiological signals to serve as the compression baseline in response to performing function fitting on the same group of physiological signals, and
   employing original physiological signals during a data cycle of the physiological signals to function as the compression baseline.

2. The method in accordance with claim 1, further comprising:
   before the grouping the physiological signals based on the sampling frequencies and/or generation mechanisms,
   identifying missing values in the physiological signals obtained, caused by artifacts;
   performing filling on the missing values; and
   attaining the sampling frequencies of the physiological signals after filling.

3. The method in accordance with claim 2, wherein the performing filling on the missing values includes
   conducting filling with respect to the missing values by using numbers.

4. The method in accordance with claim 1, wherein
   the generation mechanisms of the physiological signals generated by a same body organ and/or a same physiological activity are the same, and the physiological signals with a same mechanism belong to a same group.

5. The method in accordance with claim 1, further comprising:
   when employing the original physiological signals during the data cycle of the physiological signals to function as the compression baseline, after the data cycle of the physiological signals changes, updating the compression baseline.

6. The method in accordance with claim 5, wherein the updating the compression baseline includes
   making original physiological signals during an updated data cycle be a new compression baseline.

7. The method in accordance with claim 1, wherein the compressing, based on the grouping results, each group of physiological signals includes
   determining, based on one or more data cycles of the same group of physiological signals, a compression window corresponding to the same group of physiological signals, and compressing the same group of physiological signals according to the compression window.

8. The method in accordance with claim 7, wherein
   when the one or more data cycles of the same group of physiological signals contain only t1, a size of the compression window is determined by $n=k*t1$; and
   when one or more data cycles of the same group of physiological signals are inclusive of t1, t2 . . . , tm, the size of the compression window is determined by $n=k*[t1, t2, \ldots, tm]$, here, t1, t2, ..., tm refer to the data cycles of the same group of physiological signals; n denotes the size of the compression window; m and k are integers greater than 1; and [t1, t2, ..., tm] stands for a least common multiple of t1, t2, ..., tm.

9. A non-transitory computer-readable medium having computer-executable instructions for execution by a processor, wherein the computer-executable instructions, when executed by the processor, cause the processor to conduct the method in accordance with claim 1.

10. An apparatus for processing physiological signals, comprising:
a processor; and
a storage storing computer-executable instructions, connected to the processor,
wherein the computer-executable instructions, when executed by the processor, cause the processor to perform the method in accordance with claim 1.

11. An apparatus for processing physiological signals, comprising:
an obtainment part configured to obtain the physiological signals;
a grouping part configured to group the physiological signals based on sampling frequencies and/or generation mechanisms, so as to acquire grouping results; and
a compression part configured to compress, based on the grouping results, each group of physiological signals, the compression part including
an acquisition subpart configured to acquire a data characteristic of each group of physiological signals, and determine, based on the data characteristic, a compression baseline corresponding to a same group of physiological signals, and
a processing subpart configured to utilize the determined compression baseline corresponding to each group of physiological signals to compress the same group of physiological signals,
wherein the acquisition subpart is configured to carry out using an average or median value of the same group of physiological signals to serve as the compression baseline in response to a change in values of the same group of physiological signals within a predetermined range,
adopting a function acquired by carrying out function fitting in regard to the same group of physiological signals to serve as the compression baseline in response to performing function fitting on the same group of physiological signals, and
employing original physiological signals during a data cycle of the physiological signals to function as the compression baseline.

12. The apparatus in accordance with claim 11, further comprising:
an identification part configured to identify missing values in the physiological signals obtained, caused by artifacts;
a filling part configured to perform filling on the missing values; and
an attainment part configured to attain the sampling frequencies of the physiological signals after filling.

13. The apparatus in accordance with claim 11, wherein the compression part further includes
a compression window determination subpart configured to determine, based on one or more data cycles of each group of physiological signals, a compression window corresponding to the same group of physiological signals, and
the processing subpart is further configured to utilize the compression baseline and/or the compression window corresponding to each group of physiological signals to compress the same group of physiological signals.

* * * * *